United States Patent [19]

Kopito et al.

[11] 4,167,110

[45] Sep. 11, 1979

[54] DEVICES AND PROCESSES FOR DETERMINING PROPERTIES OF VISCOUS FLUIDS

[75] Inventors: Louis Kopito, Brookline; Samuel R. Schuster, Wellesley; Harold Kosasky, Brookline, all of Mass.

[73] Assignee: Ovutime, Inc., Newton, Mass.

[21] Appl. No.: 874,215

[22] Filed: Feb. 1, 1978

[51] Int. Cl.$^2$ .................... G01N 33/16; G01N 3/08
[52] U.S. Cl. ........................ 73/58; 73/64.4; 73/150 A
[58] Field of Search .............. 73/58, 64.4, 94, 95, 73/150 A

[56] References Cited

U.S. PATENT DOCUMENTS

| | | | |
|---|---|---|---|
| 1,231,580 | 7/1917 | Edgecomb | 73/150 R |
| 1,398,878 | 11/1921 | Michell | 73/58 |
| 1,437,730 | 12/1922 | Eberly | 73/58 |
| 1,441,564 | 1/1923 | Eberly | 73/58 |
| 1,560,662 | 11/1925 | Casey | 73/58 |
| 1,786,574 | 12/1930 | Michell | 73/58 |
| 1,920,039 | 7/1933 | Thwing | 73/150 R X |
| 1,938,975 | 12/1933 | Parks | 73/150 R |
| 1,991,854 | 2/1935 | Johansson | 73/150 A X |
| 2,049,162 | 7/1936 | Healy | 73/58 |
| 2,070,862 | 2/1937 | Healy | 73/58 |
| 2,101,322 | 12/1937 | Reed | 73/58 |
| 2,129,043 | 9/1938 | Bortsch | 73/54 X |
| 2,182,082 | 12/1939 | Hayden et al. | 73/58 |
| 2,345,968 | 4/1944 | Green | 73/58 |
| 2,406,989 | 9/1946 | Bonner et al. | 73/150 |
| 2,473,517 | 6/1949 | Freedman | 73/150 |
| 2,507,592 | 5/1950 | Euverard | 33/125 |
| 2,601,782 | 7/1952 | Foreman et al. | 73/150 |
| 2,756,587 | 7/1956 | Doble | 73/53 |
| 2,775,888 | 1/1957 | Pickup | 73/150 |
| 2,801,537 | 8/1957 | Kabelitz | 73/58 |
| 2,853,875 | 9/1958 | Alderuccio et al. | 73/150 |
| 2,865,197 | 12/1958 | Penther et al. | 73/58 |
| 2,894,388 | 7/1959 | Cook et al. | 73/58 |
| 2,963,905 | 12/1960 | Kabelitz | 73/150 |
| 3,186,221 | 6/1965 | Steib | 73/150 |
| 3,269,176 | 8/1966 | Egitto et al. | 73/150 |
| 3,282,094 | 11/1966 | Hinden | 73/150 |
| 3,415,109 | 12/1968 | Sucker et al. | 73/64.4 |
| 3,463,014 | 8/1969 | Katz et al. | 73/432 R |
| 3,741,012 | 6/1973 | Day | 73/150 A |
| 3,926,037 | 12/1975 | Kopito et al. | 73/64.4 X |

FOREIGN PATENT DOCUMENTS 1027591  2/1953  France .................... 73/58

OTHER PUBLICATIONS

Benis et al., *Adaptation of a Concentric Cylinder Rheometer to the Routine Measurement of the Viscoelastic Properties of Sputum,* in Rheology of Biological Systems, Charles C. Thomas, Publisher, Springfield, Ill., Ch. 9, pp. 218-222, 228-229, 246-247, 1973.

*Primary Examiner*—Charles A. Ruehl
*Assistant Examiner*—Joseph W. Roskos
*Attorney, Agent, or Firm*—Morse, Altman, Oates & Bello

[57] ABSTRACT

Testing of rheological properties of a fluid is performed between a pair of members having cooperating faces, each characterized by minute, randomly interspersed land portions and cavity portions. The land portions of each face are planar and are disposed geometrically in a common plane. The cavity portions are irregular and are disposed in a network subordinate to the common plane. Testing involves the steps of placing a sample of the fluid between the cooperating faces, pressing the cooperating faces into flush contact with each other, and pulling the cooperating faces from each other. The force required for rupture of the fluid within itself, without first breaking its contact with the cooperating faces, is a function of the shear stress, yield point and other rheological properties of the fluid.

26 Claims, 6 Drawing Figures

DEVICES AND PROCESSES FOR DETERMINING PROPERTIES OF VISCOUS FLUIDS

BACKGROUND OF THE INVENTION

1. Field of the Invention

The present invention relates to devices and processes for determining the physical properties of Newtonian and non-Newtonian fluids, and, more particularly, to the testing of fluids by relatively movable mechanical elements in contact therewith.

2. The Prior Art

Various instruments have been proposed for testing viscoelastic properties of fluids, including surface tension, viscosity, shear stress, and yield point. Certain of such instruments involve relatively movable elements having bearing surfaces between which the fluid to be tested is placed. In each case, the force required to cause movement between the fluid-contacting elements is a function of the fluid's rheological properties. In such instruments, related difficulties are encountered in establishing reproducible test conditions and reproducibly maintaining the sample. Particularly in the case of non-Newtonian (i.e. non-ideal), multiphase polymeric fluids, such as milk, ketchup, mustard, blood, mucus, and saliva, the steps of pressing, shearing, separating, etc. cause homogenization, drying, etc.

SUMMARY OF THE INVENTION

The primary object of the present invention is to provide devices and processes, in which reproducible conditions in a fluid sample, particularly a non-Newtonian fluid sample, are maintained, while its rheological properties, particularly its shear stress and yield point, are being tested, by virtue of a pair of members having cooperating faces, each characterized by minute land portions and minute cavity portions, which are randomly interspersed. The land portions are planar and are disposed geometrically in a common plane. The cavity portions are irregular and are disposed in a random network subordinate to the common plane. Testing involves the steps of placing a sample of the fluid between the cooperating faces, applying a compressive force by which the cooperating faces are urged toward each other until their land portions are in flush contact and the fluid is distributed within the cavity network, and applying a tensile force at a fixed or variable separation rate, by which the cooperating faces are urged away from each other until rupture within the fluid occurs. The arrangement is such that reproducible conditions in the fluid are maintained during the application of the compressive and tensile forces and selected rheological properties of the fluid are indicated as a function of the tensile force at the instant of parting. These selected rheological properties relate to tackiness, i.e. the yield stress or yield point of the sample, rather than to the surface tension or adhesive attraction of the sample, as would be the case if separation were to occur between the sample and one or both of the cooperating mechanical faces.

Other objects of the present invention will in part be obvious and will in part appear hereinafter.

The invention accordingly comprises the devices and processes, together with their parts, steps, and interrelationships, which are exemplified in the following disclosure, the scope of which will be indicated in the appended claims.

BRIEF DESCRIPTION OF THE DRAWINGS

For a fuller understanding of the nature and objects of the present invention, reference is made to the following detailed description, which is to be taken in connection with the accompanying drawings, wherein.

DETAILED DESCRIPTION OF THE PREFERRED EMBODIMENT

Figure 1:
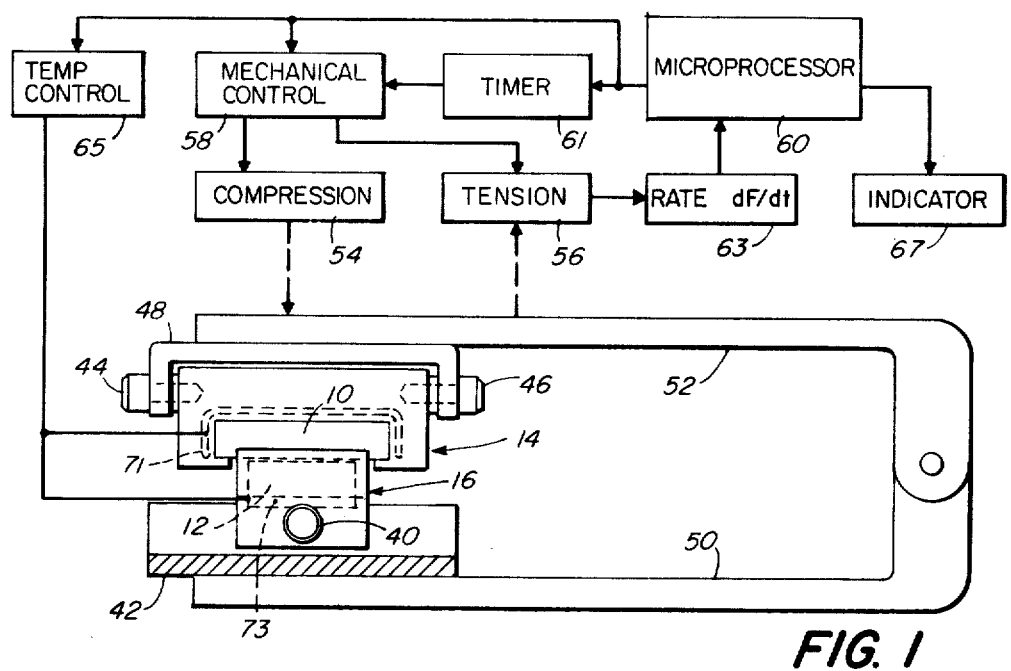
FIG. 1 is a schematic view of a device embodying the present invention, showing a broken-away side elevation of the test components and a block diagram of the control components.
Figure 2:
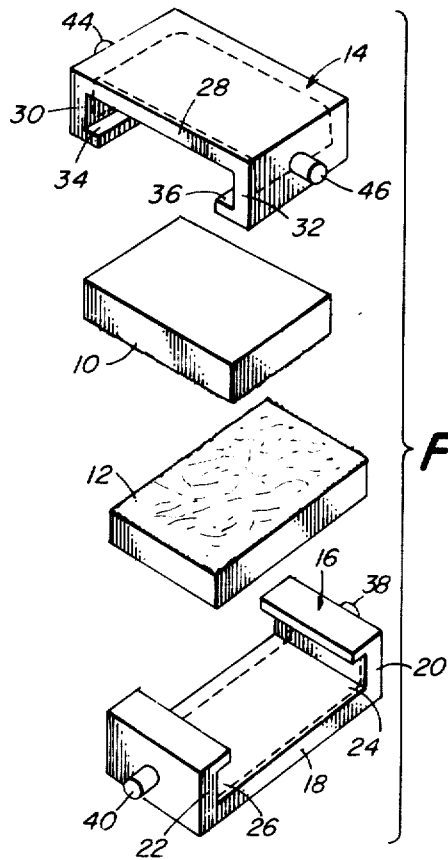
FIG. 2 is an exploded perspective view of the test components.
Figure 3:
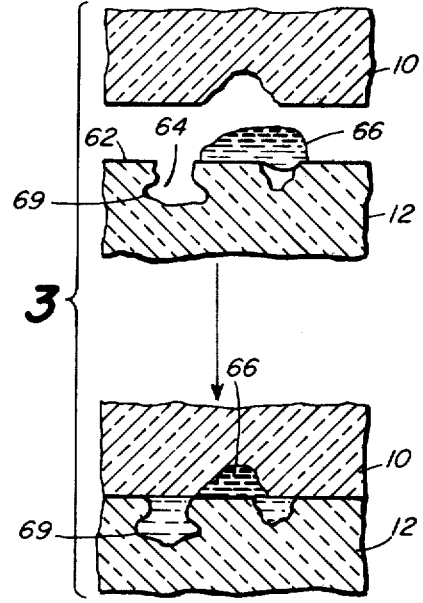
FIG. 3 is an exaggerated cross-sectional view of portions of the test components, performing steps of a process of the present invention.

Generally, the illustrated embodiment of the present invention comprises a pair of disposable test elements 10, 12, which are shown in elevation in FIG. 1, in perspective in FIG. 2, and in exaggerated cross section in FIG. 3. These test elements are composed of a rigid solid, for example, a vitreous material such as glass, a metal such as stainless steel, or a polymer such as methyl methacrylate, characterized by co-planar lands and subordinate cavities, which will be described in greater detail below. These test elements are carried by a pair of test holders 14, 16, which are constrained for reciprocating and gimbaled motion with respect to each other.

Lower test holder 16 has a supporting base portion 18 and a pair of undercut edge portions 20, 22, which provide a pair of slots 24, 26 for the reception, retention, and removal of test element 12. The length of test element 12 is approximately the same as the distance between the walls of slots 24, 26. The thickness of test element 12 is approximately the same as the height of slots 24, 26. The width of test element 12 is approximately the same as the width of test holder 16. There are sufficient dimensional tolerances to permit test element 12 to slide easily into a snug seat on base portion 18, with its ends within slots 24, 26, and to permit test element 12 to slide easily from this seat for replacement, by convenient manipulation. Upper test holder 14 has a supporting base portion 28 and a pair of undercut edge portions 30, 32, which provide a pair of slots 34, 36 for the reception, retention, and removal of test element 10. The dimensions of test element 10 are the same as those of test element 12 and the dimensions of the various portions of test holder 16. Thus test elements 10, 12 are interchangeable and disposable. It will be observed that the distance between edge portions 20, 22 is greater than the width of test element 10 and that the distance between edge portions 30, 32 is greater than the width of test element 12. The arrangement is such that, when the test holders are longitudinally at right angles with respect to each other, they clear each so that medial portions of test elements 10, 12 are movable into flush contact with each other. Preferably, test holders 14, 16, as well as the remaining elements other than test elements 10, 12, are composed of a metal such as aluminum. The composition and configuration of test elements 10, 12 will be specified below.

Extending into holes in edge portions 20, 22 of test holder 16 are axially aligned pair of pins 38, 40. Test holder 16 is carried by a lower support 42, which provides gimbal journals in which pins 38, 40 are seated. Extending into holes in edge portions 30, 32 of test holder 14 are axially aligned pair of pins 44, 46. Test holder 14 is carried by an upper support 48, which provides gimbal journals in which pins 44, 46 are seated. Thus test holders 14, 15 rock about perpendicular axes in such a way that the inner faces of test elements 10, 12 can adjust to flush contact as they are pressed against each other. As shown, lower support 42 is held by an arm 50, which is fixed to a base support, and upper support 48 is held by an arm 52, which is pivoted to arm 50. Support 48 is pressed downwardly by a suitable compression mechanism 54 and is pulled upwardly by a suitable tension mechanism 56. A suitable control 58 operates compression mechanism 64 and tension mechanism 56 in a sequence that is governed by a microprocessor 60, in association with a timer 61, a ratemeter 63, a temperature control 65, and an indicator 67, all of which will be described in greater detail below.

EXAMPLE I

Figure 4:
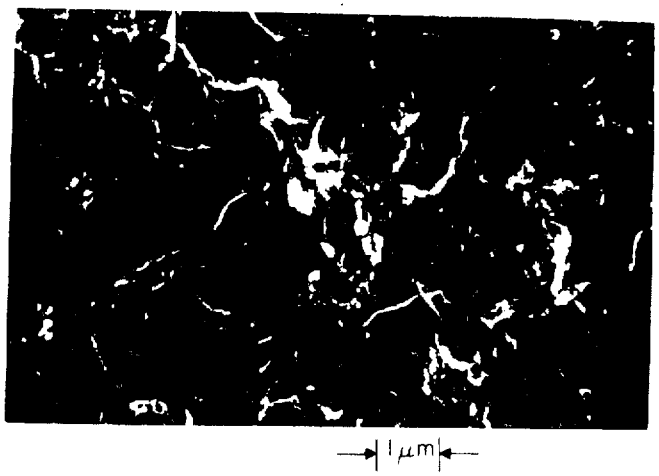
FIG. 4 is a photographic reproduction of an electron microscope display of the face of a test element embodying the present invention.
Figure 5:
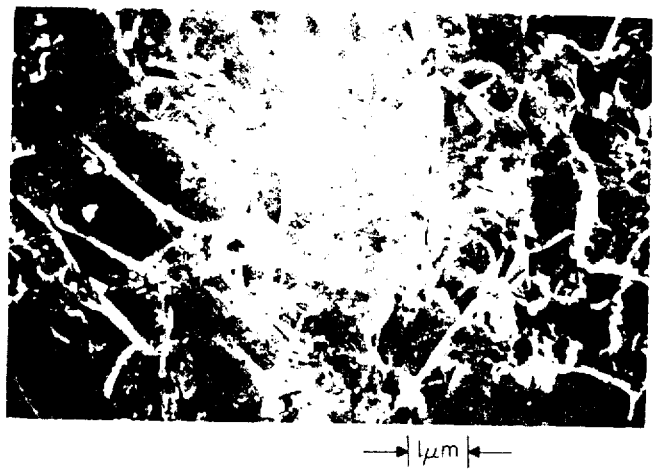
FIG. 5 is a photographic reproduction of an electron microscope display of the face of another test element embodying the present invention.
Figure 6:
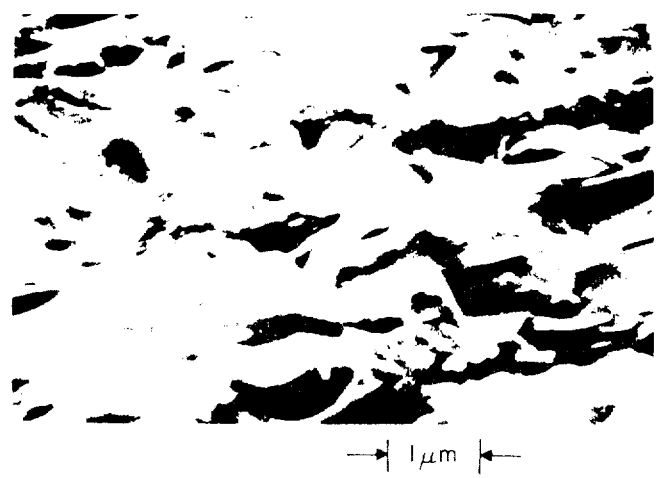
FIG. 6 is a photographic reproduction of an electron microscope display of the face of another test element embodying the present invention.

In one preferred embodiment, as shown in FIG. 3, test elements 10, 12 initially are composed of transparent glass and their inner surfaces are subjected to intense but limited sand blasting, such that: (1) much of the flat surface remains intact in the form of flat lands 62, which are disposed along their original geometrical plane; and (2) much of the rest of the surface is irregularly pitted, to define a cavity network 64 interspersed among the lands. As shown at 69, some or all of the cavities have lower boundaries which undercut lands 62. FIGS. 5 and 6 are electron microscope photographs of two alternative surfaces embodying the present invention. The lands appear dark because they correspond to exposure by specular radiation. The cavities appear white because they correspond to exposure by diffuse radiation. It has been found that the ratio of area of lands to total area of the test element face is approximately equal to the percentage transmittance of light through the element. It has been found that the ratio of area of cavities to total area of the test element face is approximately equal to the percentage reflectance of light from the element. Preferably, the percentage of lands to total area ranges from 3 to 80% and the percentage of cavities to total area ranges from 80 to 3%. The glass face of FIG. 4 is relatively moderately abraded. The glass face of FIG. 5 is relatively heavily abraded. It will be observed, however, that both faces have at least some well distributed lands with dimensions of more than 0.0001 mm (1 micron).

EXAMPLE II

In another preferred embodiment, test elements 10, 12 are composed of stainless steel and are characterized by a working face with randomly interspersed lands and cavities that correspond to those of the elements of Example I. This face is formed by coating a stainless steel blank with a photoresist mask, photoexposing the mask to an image of a selected working face of the type shown in FIGS. 4 and 5, conditioning the resulting photoexposed mask with a caustic rinse, etching the masked face in an acid such as sulfuric acid, and dissolving the mask in a cleansing bath.

OPERATION

In operation, a non-Newtonian fluid sample is placed between the inner faces of elements 10, 12 as shown in FIG. 3. Next, timer 61 is triggered and, under the constraint of compression mechanism 54, upper support 48 is pressed downwardly toward lower support 42 in such a way that test holders 14, 16 rock about their axes until the inner surfaces of lands 62 of test elements 10, 12 are virtually flush and virtually in contact with each other along a single geometrical plane. Under these conditions the cavity networks of the faces of elements 10, 12 communicate, with most (say at least 95%) of the fluid distributed therein. Next, under the constraint of tension mechanism 56, upper support 48 is pulled upwardly away from lower support 42, the tensile force being increased at a predeterminedly selected rate, dF/dt. At the moment the interior of the fluid distribution ruptures, indicator 60 provides a reading, which corresponds to the yield stress or yield point of the fluid. During the compression step, the random distributions of lands and cavities on the working faces preclude any mechanical locking of these faces to each other. A temperature control 65 operates a pair of thermoelectric heating-cooling assemblages 71, 73 in holders 14, 16 in order to maintain a reproducible thermal environment for the sample being tested. During the tension step, separation of the sample from the element surface is prevented in part by undercut regions 69 of cavities 64. The overall system is governed by microprocessor 60 and mechanical control 58.

It has been found that the chemical composition of the surfaces of lands 62 and cavities 64 may be selected for specific results with specific fluids. In one embodiment, lands 62 and cavities 64 are in their original uncoated condition. In a second embodiment, lands 62 and cavities 64 are coated with an extremely thin coating, i.e. solid, liquid, fibrous, elastomeric, that is capable of absortive, chemical, enzymatic, or physicochemical interaction with the sample. One such coating, for example, can be produced by dipping the test element in a 1% solution of silicone in an organic solvent such as xylene, toulene, or acetone. The aforementioned second embodiment is particularly adapted for determining the rheological properties of cervical mucus as an indication of presence or absence of ovulation.

The prevent invention thus enables closely reproducible test conditions until the moment of rupture. Since certain changes may be made in the foregoing disclosure without departing from the scope of the invention hereof, it is intended that all matter descsribed in the foregoing specification or shown in the accompanying drawings be interpreted in an illustrative and not in a limiting sense.

What is claimed is:

1. A device for testing the properties of a fluid, said device comprising:
   (a) a pair of disposable test elements for presenting a pair of faces that are adapted for relative movement between remote locations at which said faces are apart and proximate locations at which said faces are in flush contact with each other;
   (b) said faces having a pair of distributions of lands and cavities;

(c) said pair of distributions of lands of said faces being planar and being disposed geometrically in a pair of common planes;
(d) said pair of distributions of cavities of said faces being subordinate to said pair of common planes to form a pair of cavity networks;
(e) means for reciprocating said solid faces into and out of said flush contact with each other;
(f) portions of said pair of distributions of lands being in substantial contact with each other when said faces are in said flush contact with each other;
(g) said pair of cavity networks forming a composite network when said faces are in said flush contact with each other;
(h) whereby a small sample of said fluid between said faces is spread in said composite network during said movement into said proximate locations and the force associated with said movement into said remote locations is indicative of properties of said fluid.

2. The device of claim 1 wherein each of said pair of distributions is random.

3. The device of claim 1 wherein said lands are of varying sizes.

4. The device of claim 1 wherein the percentage area of lands of each face to total area of each face ranges from 3 to 80%.

5. The device of claim 1 wherein the percentage area of cavities of each face to total area of each face ranges from 80 to 3%.

6. The device of claim 1 wherein at least some of said lands of each face have a maximum dimension of at least 0.001 mm.

7. The device of claim 1 wherein the free surface of said lands and said cavities is composed of a vitreous material.

8. The device of claim 1 wherein the free surface of said lands and said cavities is composed of a metal.

9. The device of claim 1 wherein the free surface of said lands and said cavities is composed of a polymer.

10. The device of claim 1 wherein the configuration of said lands and said cavities of each face is determined by a solid substrate of a first composition and the free surface of said lands and said cavities of each face is coated with a relatively thin layer of another composition.

11. The device of claim 10 wherein said other composition is a silicone.

12. A device for testing the properties of a fluid, said device comprising:
(a) a first test holder and a second test holder constrained for reciprocable motion with respect to each other;
(b) said first test holder defining a first seat for a first test element;
(c) said second test holder defining a second seat for a second test element;
(d) means for gimbaling said first test holder and said second test holder with respect to each other; and
(e) said first test holder and said second test holder clearing each other when said first test holder and said second test holder are in their innermost relative positions.

13. A device for testing the properties of a fluid, said device comprising:
(a) a first test holder and a second test holder constrained for reciprocable motion with respect to each other;
(b) said first test holder defining a first seat for a first test element;
(c) said second test holder defining a second seat for a second test element;
(d) means for gimbaling said first test holder and said second test holder with respect to each other universally;
(e) said first test holder and said second test holder clearing each other when said first test holder, and said second test holder are in their innermost relative positions;
(f) a pair of disposable test elements for presenting a pair of solid faces that are adapted for movement between remote locations at which said faces are apart and proximate locations at which said faces are flush with each other;
(g) each of said faces having a distribution of interspersed lands and cavities;
(h) said lands of each of said faces being planar and being disposed geometrically in a common plane;
(i) said cavities of each of said faces communicating with each other subordinately to said common plane;
(j) one of said test means being held in said first test holder; and
(k) the other of said test means being held in said second test holder.

14. The device of claim 13 wherein said distribution is random.

15. The device of claim 13 wherein said lands are of varying sizes.

16. The device of claim 13 wherein the percentage area of cavities of each face to total area of each face ranges from 3 to 80%.

17. The device of claim 13 wherein the percentage area of cavities of each face to total area of each face ranges from 80 to 3%.

18. The device of claim 13 wherein at least some of said lands of each face have a maximum dimension of at least 0.001 mm.

19. The device of claim 13 wherein the free surface of said lands and said cavities is composed of a vitreous material.

20. The device of claim 13 wherein the free surface of said lands and said cavities is composed of a metal.

21. The device of claim 13 wherein the free surface of said lands and said cavities is composed of a polymer.

22. The device of claim 13 wherein the configuration of said lands and said cavities of each face is determined by a solid substrate of one composition and the free surface of said lands and said cavities of each face is coated with a relatively thin layer of another composition.

23. The device of claim 22 wherein said second composition is a silicone.

24. A process for testing the rheological properties of a fluid sample, said process comprising the steps of:
(a) disposing said fluid sample between a pair of test elements having a pair of test faces;
(b) each of said test faces having interspersed lands and cavities;
(c) said lands of each of said faces being planar and being disposed geometrically in a common plane;
(d) said cavities of each of said faces being subordinate to said common plane;
(e) urging said test faces into flush contact such that said lands of both of said test faces are disposed substantially in a single common plane and most of said fluid sample is disposed in said cavities;

(f) exerting an increasing pulling force tending to separate said test faces from each other in order to cause rupture of said fluid sample at a particular time; and (g) measuring said pulling force at said particular time.

25. The process of claim 24 wherein said fluid sample is cervical mucus.

26. Disposable test elements for measuring properties of a fluid:

(a) a pair of said test elements presenting a pair of faces that are adapted for relative movement between remote locations at which said faces are apart and proximate locations at which said faces are in flush contact with each other;

(b) said faces having a pair of distributions of lands and cavities;

(c) said pair of distributions of lands of said faces being planar and being disposed geometrically in a pair of common planes;

(d) said pair of distributions of cavities of said faces being subordinate to said pair of common planes to form a pair of cavity networks;

(e) portions of said pairs of distributions of lands being in substantial contact with each other when said faces are in said flush contact with each other;

(f) said pair of cavity networks forming a composite network when said faces are in said flush contact with each other;

(g) whereby a small sample of said fluid between said faces is spread in said composite network during said movement into said proximate locations and the force associated with said movement into said remote locations is indicative of properties of said fluid.

* * * * *